(12) United States Patent
Miller (10) Patent No.: US 7,263,998 B2
(45) Date of Patent: Sep. 4, 2007

(54) RESPIRATORY APPARATUS

(75) Inventor: Donald Munro Miller, Cape Town (ZA)

(73) Assignee: Slipa Enterprises (BVI) Limited, Tortola (VG)

( * ) Notice: Subject to any disclaimer, the term of this patent is extended or adjusted under 35 U.S.C. 154(b) by 244 days.

(21) Appl. No.: 10/332,590

(22) PCT Filed: Jul. 13, 2001

(86) PCT No.: PCT/ZA01/00093

§ 371 (c)(1),
(2), (4) Date: Jan. 9, 2003

(87) PCT Pub. No.: WO02/32490

PCT Pub. Date: Apr. 25, 2002

(65) Prior Publication Data

US 2003/0172935 A1    Sep. 18, 2003

(51) Int. Cl.
*A61M 16/00*    (2006.01)

(52) U.S. Cl. ............................. 128/207.15; 128/207.14

(58) Field of Classification Search ........... 128/207.14, 128/207.15
See application file for complete search history.

(56) References Cited

U.S. PATENT DOCUMENTS

| | | | | |
|---|---|---|---|---|
| 5,038,766 A | | 8/1991 | Parker | ................... 128/200.26 |
| 5,443,063 A | * | 8/1995 | Greenberg | ............. 128/207.15 |
| 5,513,627 A | | 5/1996 | Flam | ..................... 128/200.26 |
| 5,632,271 A | * | 5/1997 | Brain | ..................... 128/207.15 |
| 5,653,229 A | * | 8/1997 | Greenberg | ............. 128/207.15 |
| 5,853,004 A | | 12/1998 | Goodman | ............. 128/207.15 |
| 5,878,745 A | * | 3/1999 | Brain | ..................... 128/207.15 |
| 5,988,167 A | | 11/1999 | Kamen | ................... 128/207.15 |
| 6,070,581 A | | 6/2000 | Augustine | .............. 128/207.15 |
| 6,119,695 A | * | 9/2000 | Augustine et al. | ..... 128/207.15 |
| 6,152,136 A | * | 11/2000 | Pagan | .................... 128/207.15 |
| 6,386,199 B1 | * | 5/2002 | Alfery | .................... 128/207.15 |

FOREIGN PATENT DOCUMENTS

WO    9816273    4/1998

* cited by examiner

*Primary Examiner*—Anhtuan T. Nguyen
*Assistant Examiner*—Darwin P Erezo
(74) *Attorney, Agent, or Firm*—Ladas & Parry LLP (57) ABSTRACT

An artificial airway device (10) of a resilient material for use as a combined obturator and airway device without penetration into a larynx comprising a pre-formed flexible saccular chamber (14) and having a semi-rigid hollow stem (14) projecting from a position at or near one end of the chamber at an obtuse angle and capable of being flexed into a curve that deviates up to 90 degrees from the longitudinal axis of the said chamber, the chamber being provided with one or more openings, and dimensioned and arranged so that in use the chamber is adapted to sealingly engage in a patient's pharynx with at least one opening in communication with the patient's laryngeal inlet and the stem extends into or through the patient's mouth for connection to a breathing circuit.

17 Claims, 5 Drawing Sheets

RESPIRATORY APPARATUS

SCOPE OF THE INVENTION

The present invention relates to respiratory apparatus in the form of an artificial airway device for placement into the oropharynx of an unconscious patient to maintain airway patency, to permit attachment to respiratory apparatus, to permit either spontaneous or controlled positive pressure ventilation and to prevent the inhalation into the lungs of extraneous matter such as vomitus or blood.

THE STATE OF THE ART

An unconscious patient may have need of some or all four of the above objectives for supporting respiration and, therefore, life. During anaesthesia or resuscitation this may be achieved by means of an endotracheal tube with an inflatable cuff around the end which is placed within the trachea, or a laryngeal mask airway (LMA), which also involves the use of an inflatable cuff at the end of a tube, the end of which is placed around the entrance to the larynx and within the pharynx, or an oesophageal obstructor airway (EOA) named "Combitube" or derivative. This comprises a double lumen double cuffed tube, the longer tube with attached cuff passes into the oesophagus for the purpose of sealing and isolating contents which may enter the oesophagus from below or to prevent the escape of gas under pressure from above from entering the stomach. The shorter tube for ventilating the lungs ends within the pharynx, the oro-nasal outlet from the pharynx being sealed off within the pharynx by means of the second cuff which surrounds both tubes, which when inflated allows for positive pressure to develop within the pharynx. Sometimes, an oral or nasal airway tube for preventing obstruction of the airway is used in combination with a facemask.

More recently a cuffed oro-pharyngeal airway (COPA) has been introduced by Mallinekrodt Medical, Inc, U.S. Pat. No. 5,743,256, (May 30, 1995) which can be used to achieve 3 of the four objectives stated above but fails to protect the lungs from extraneous matter that enters the pharynx from entering the lungs. The Glottic aperture seal airway of Augustine Medical Inc. PCT publication number: WO 98/16273, purports to achieve this advantage, however, it is not as reliable as was originally hoped. Numerous other double cuff inflating devices are appearing in the current market and may be classed as derivatives of the EOA and COPA above, e.g. that of Sato et al U.S. Pat. No. 5,743,258 (Apr. 28, 1998).

The maximum inflation pressure that can be used before gas leakage occurs around the cuffs limits the application of controlled ventilation by the latter two methods. They also run the risk of inflating the stomach and do not provide a secure airway from the possible aspiration of vomitus. The LMA provides a partial seal of the oesophagus but regurgitation if it gets past the seal is more likely to pass into the inflatable bag cavity in the case of the LMA from whence the contents are easily funneled into the larynx. The COPA does not provide any seal of the oesophagus. The Combitube would appear to be an effective device, for controlled ventilation, sealing off the oesophagus, but its correct placement can pose problems, either too deep or not deep enough. It is also rather elaborate and expensive. The LMA would appear to be ideal except for the fact that the pressures that can be generated in controlled ventilation are limited as the mask could be dislodged at higher inflation pressures. In addition, although it is partially effective in isolating the airway from extraneous matter in the pharynx, should any extraneous matter enter the lumen of the mask, which does not provide a high quality isolation of the trachea from pharyngeal matter, it will tend to be funneled into the larynx. To overcome this disadvantage an improved LMA named the 'Proseal' LMA incorporates a moderate bore tube for removing liquid that may accumulate in the mask region of the airway by suction or siphonage and is disclosed in Japanese Patent No. 2-283378 (Nov. 20, 1990). The placement in the trachea of the endotracheal tube is the most effective means of achieving all four of the above objectives, however, its use requires experience, skill and the use of a laryngoscope which in turn has its own unwanted side effects consequent upon powerful neural reflex actions. Its placement may also require the use of muscle relaxing drugs.

It is an objective of the present invention to provide an appropriately shaped artificial airway which will obviate the need for a cuff-blowing up mechanism for sealing purposes and yet one that retains most of the advantages of the use of endotracheal tubes, Combitubes or laryngeal masks in the above mentioned circumstances and to avoid, as far as it is possible, their individual disadvantages.

DESCRIPTION

In accordance with the invention, an artificial airway device of a resilient material for use as a combined obturator and airway device without penetration into the larynx comprises a flexible pre-formed shaped saccular chamber designed to seal in the pharynx at the base of the tongue and having a semi-rigid hollow stem projecting from a position at or near one end of the chamber at an obtuse angle (i.e. 90° to 180°) to the longitudinal axis of the said chamber. The chamber is provided with one or more openings, and is dimensioned and arranged so that in use it is adapted to sealingly engage in a patient's pharynx with at least one opening communicating with the patient's laryngeal inlet. The stem extends into or through the patient's mouth for connection to a breathing circuit.

In order to facilitate the description of the device, the surfaces which are referred to herein as 'upper' and 'lower' are those which respectively are upper and lower when the device is in use in a patient lying on his back, or as viewed as a foot with its sole lowermost.

The saccular chamber is preferably of a generally rounded foot-shape with the rounded narrow part of the foot having its under face slightly angled, preferably about 15° to the longitudinal axis of the chamber, to ease insertion of the device into a patient's pharynx. The upper face of the chamber is preferably of a substantially concave form and is provided with a transverse ridge with a pair of lateral lumps to act as a sealing area which in use is arranged to conform with a patient's pyriform fossae and produce a seal with the pharyngeal walls at the base of the tongue. The hollow stem forms a flexible junction with the wider part of the foot, which when flexed does not distort the shape of the sealing portion of the chamber.

The generally foot-shaped saccular chamber may additionally be provided with a bulb or lobe as a 'heel' extending beyond the stem and so dimensioned and arranged so that in use it engages into the patient's nasal-pharynx in order to hold the device in the required position.

The relative stiffness of the stem compared with that of the chamber may cause the chamber to buckle resiliently at the foot of the stem when the stem is turned towards the perpendicular. In use however the design is such that the shape of the part of the chamber that would make contact with the pharyngeal wall and the nasal pharynx is retained.

The upper face of the chamber between the 'toe' end of the chamber and the ridge with the two lumps is preferably concave along its length or crescent-shaped in cross-section in order to better conform with the shape of a patient's pharynx. This shape decreases the chance of the toe catching the epiglottis at insertion. The toe protrudes beyond the laryngeal opening so that in use it extends into the entrance of the oesophagus where it provides a seal in order to prevent any gas from entering the stomach.

Two openings are provided on the forward face so that in use they are arranged to collect any liquid in the blind end of the chamber and thus in use prevent any liquid from entering the patient's larynx, trachea or lungs. Liquid can be removed from the chamber as required by aspirating it through a catheter inserted into the chamber.

A vertical ridge between the said two openings may be provided on the upper face of the foot so that in use it is arranged to both hold the epiglottis away from the opening and will maintain resilience of the ridge between the said two 'lateral lumps'. The resilience of the ridge is important to prevent the base of the tongue moving towards the posterior pharyngeal wall as this movement is associated with the epiglottis closing against the laryngeal opening (or glottis).

The device will now be described in greater detail in relation to its preferred method of use. This is a type of pharyngeal outlet obturator airway-(POOBAIR),and may include the standard 15 mm tapered attachment connector inserted into or over the end of the said hollow stem for attachment to breathing apparatus; said stem extending through the mouth, where it may bend to conform to the gentle curved shape of the tongue pushing against the hard palate, to the said saccular foot-shaped chamber portion that is located in the pharynx, with longitudinal axis approximately at right angles to the stem at the entrance to the mouth, the bend at the junction of stem with chamber as it hooks into the base of the tongue and expands to form an upward-outlet-from-the-pharynx gas tight seal (the said obturator function) in the space that extends from the base of the tongue or glossoepiglottic fold and the two lateral pyriform fossae or valleculae in the anterior aspect, and in a crescent shaped arc seals at the same level against the lateral and posterior pharyngeal walls. The opening in the front of the chamber corresponds with the laryngeal opening for the passage of gas to flow between the larynx and the airway device. The said saccular chamber may be extended further and with benefit include each or all of:

a) a rounded extension of the saccular chamber for the purpose of protruding into the entrance of the oesophagus to seal the "downward" outlet from the pharynx into the oesophagus thereby closing off all outlets, obturating downward and upward outlets from the pharynx except via the chamber and stem open ends of the device. The blind downward obturating toe of the foot along with the hollow chamber also provides a means of collecting secretions within the device.

b) an upward extension of the chamber to incorporate a heel-shape that corresponds to the nasopharynx and soft palate for the purpose of ensuring a more stable location of the sealing airway in the pharynx by anchoring the said device in its position in the pharynx as it settles into the nasopharynx and soft palate in such a way as to prevent expulsion as the airway pressure rises.

Accordingly, one common characteristic in the above existing artificial airway devices is the need for an inflatable cuff to expand into the right size pharyngeal cavity. In devices in accordance with the invention, this is obviated because they are supplied in a variety of sizes typically seven, so that the appropriate size to be chosen may specifically match the size of each prospective patient's pharyngeal cavity.

DESCRIPTION RELATING THE INVENTION MORE SPECIFICALLY TO THE ENCLOSED NUMBERED DRAWINGS

The invention will now be specifically described by way of example with reference to the accompanying drawings, in which FIGS. 1 to 5 show one embodiment of the invention, FIGS. 6 to 8 show another embodiment of the invention;

FIGS. 9 to 11 show another embodiment of the invention and

FIGS. 12 to 15 show two embodiments adapted to allow for an unusual or enlarged pharyngeal tonsillar anatomy.

FIGS. 1 to 5 show an artificial airway device 10 for use as a combined obturator and airway device without penetration into the larynx shaped and pre-formed of a resilient material. It comprises a flexible saccular chamber 14 and has a semi-rigid hollow stem 12 projecting from a position at or near one end of the chamber 14 with junction between the stem 12 and the chamber 14 at 19. The stem 12 is set at about 45° to the longitudinal axis of the chamber 14 and can be flexed into a curve that deviates up to 90 degrees from the said longitudinal axis. The chamber has one or more openings 13, shown here as two vertical slits.

The device exists in a range of different sizes to fit patients from a child to a large adult. In use the anaesthetist will select a suitably dimensioned device, generally by measuring the patient's thyroid cartilage and choosing a matching diameter for the device, so that in use the chamber 14 is adapted to sealingly engage in the patient's pharynx with at least one opening 13 communicating with the patient's laryngeal inlet. The stem 12 extends into or through the patient's mouth for connection to a breathing circuit via an adaptor 40 at its open end 11.

The saccular chamber 14 is of a generally a rounded foot-shape, with the 'toe' part 20 of the foot having a lower face 21 slightly angled, preferably about 15° to the longitudinal axis of the chamber 14, to ease insertion of the device into a patient's pharynx. The chamber is provided with a ridge 25 on its upper face extending to a pair of lateral lumps 24 and a substantially convex-planar lower face 30 to produce a sealing zone so that at this point the shape of the chamber is adapted to conform substantially with a patient's pharyngeal walls at the base of the tongue.

The hollow stem 12 forms a flexible junction with chamber at 19, so that when it is flexed it does not distort the shape of the sealing portion of the chamber between the ridge, the lateral lumps 24 and the rounded under-side of the chamber. The lumps 24 are adapted to conform with the patient's pyriform fossae to act as an anchoring means at the base of the tongue and to keep the base of the tongue from the posterior pharyngeal wall when in use.

The general foot shape is completed (FIGS. 1-5) by a bulb or lobe 26 extending beyond the stem to form a heel. In use (FIG. 5), the lobe 26 is so dimensioned and arranged that it engages into the patient's nasal-pharynx in order to hold the device in the required position. The relative stiffness of the stem 12 compared with the chamber causes the chamber to buckle resiliently at the foot of the stem 19 when the stem is turned towards the perpendicular to the longitudinal axis of the chamber, notwithstanding that in use the shape of the sealing zone around the ridge is maintained in contact with the pharyngeal wall and the lobe 26 remains engaged in the nasal pharynx.

The ridge 25 in the front between the said lateral lumps 24 is sufficiently resilient so that in use it holds the epiglottis away from the laryngeal opening. To increase the resilience of the chamber 14 and its resistance to collapse at the level of the said ridge, 24 and 25, and thus to facilitate the holding the base of the tongue away from the posterior pharyngeal wall, indentations on both surfaces on either side of the ridge are provided. In use, these indentations will abut their opposite numbers 31 with 15 and 32 with 16, to provide the desired stiffness, yet allowing sufficient flexibility for the chamber to comfortably adapt to the patient's pharynx and avoiding subsequent irritation to the throat.

Figure 5:
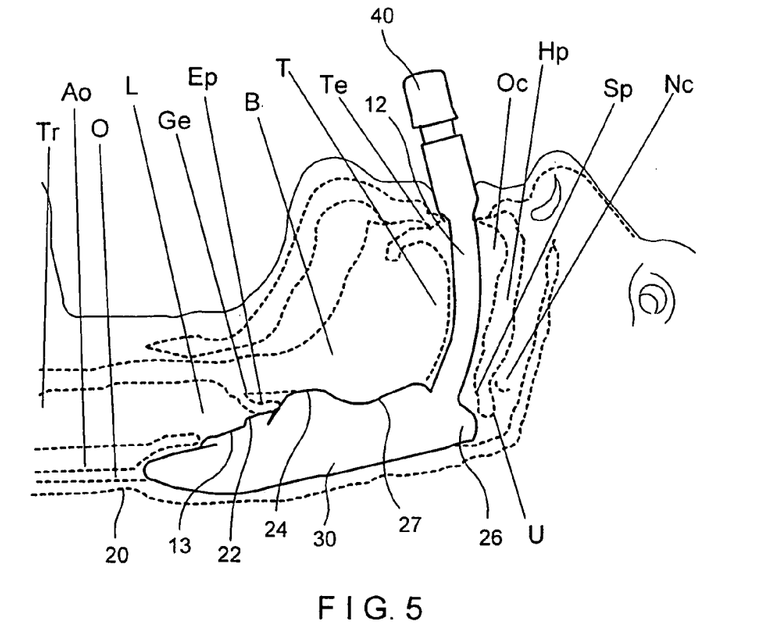
FIG. 5 is a sectional side elevation of the device in relation to the anatomy of a patient.

In use as shown in FIG. 5 The tip of the rounded foot shaped or 'toe' end 20 of the chamber is dimensioned so that it protrudes beyond the laryngeal opening sealing the oesophagus O in order to prevent gas from entering the stomach.

The two openings 13 in addition to providing the airway connection with the patient's laryngeal opening are arranged to collect by gravity any liquid in the bottom of the chamber 14 and thus in use prevent the liquid from entering the patient's larynx, trachea or lungs.

A longitudinal bar 16 between the two openings 13 is provided on the upper face of the chamber so that in use it is arranged to both hold the epiglottis away from the opening and to contribute to the stiffness of the ridge 25 between the two lumps 24. Additionally, this helps the ridge to perform one of its main functions, namely, to keep the base of the tongue away from the posterior pharyngeal wall. The bar 16 also acts as a barrier to a catheter which may be used to aspirate liquid from the chamber during use and prevents it from entering the larynx.

The upper surface of the chamber 14 between the ridge 25 and the stem is in the form of a hollow 27. When in position, the hollow 27 receives the posterior portion of the tongue with the lumps 24 and the ridge 25 hooked around the base of the tongue.

The upper face of the toe end of the chamber 14 is provided with a pair of lateral ribs 22 with a gentle indentation 23 where they respectively join the lumps 24. This serves the purpose of the device better conforming to anatomical accuracy, when in use, with the said gentle indentation 23 corresponding to pharyngeal mucosa that overlies the cricoid cartilage. This is to decrease pressure on the pharyngeal mucosa at this site, in order to lower the incidence of sore throats.

The saccular chamber thus fits precisely into the shape of the pharynx and with the stem bent to form almost a right angled bend at the junction 19. Airway pressure that may rise during positive pressure ventilation would tend to push the device in the direction of the nasopharyngeal cavity Nc but is held in position by the heel 26, thus preventing it from being dislodged. When it is desirable to remove the device, this may be achieved by pulling on the stem 12, which automatically dislodges 26 in an appropriate direction from the soft palate Sp and nasopharyngeal cavity Nc.

It may also be appreciated that should secretions or stomach contents accumulate in the pharynx for any reason, the two openings 13 provide a means for allowing pharyngeal secretions to flow into the saccular chamber 14 of the hollow device 10 providing a 'sump' means for the collection of the liquid. This can be aspirated by means of a suction catheter that may be passed via the end 11 and stem 12 at a convenient time.

Figure 1:
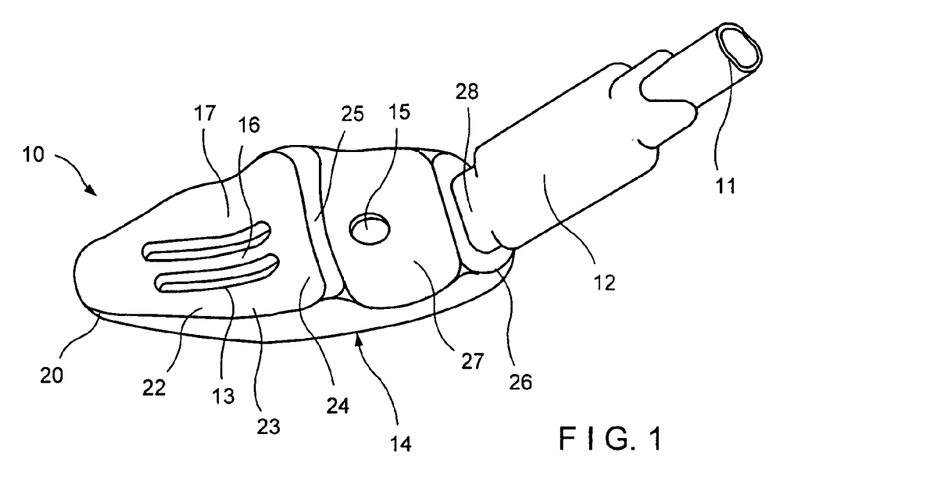
FIG. 1 is a perspective view of an airway device in accordance with the invention from above.
Figure 2:
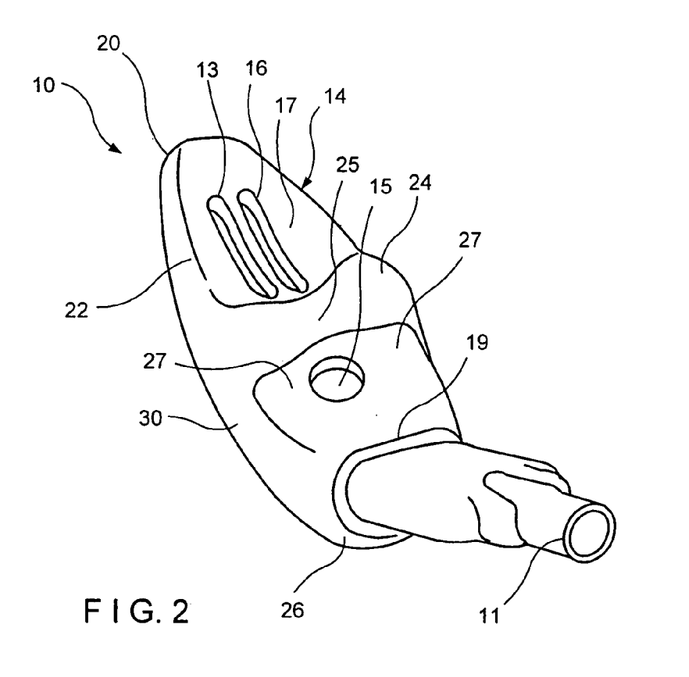
FIG. 2 is another perspective view from above.
Figure 3:
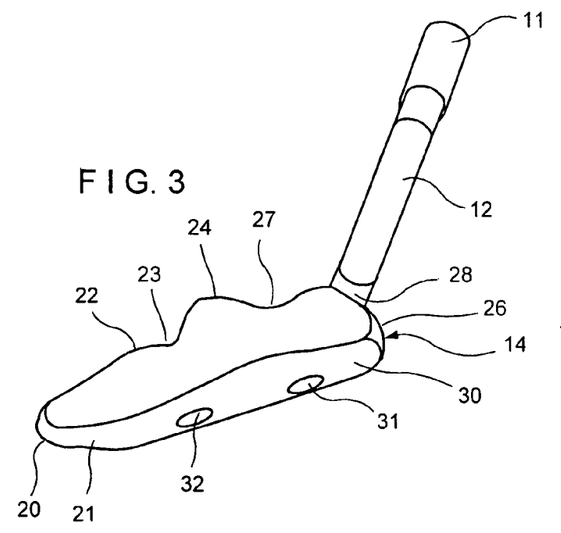
FIG. 3 is a side elevation.
Figure 4:
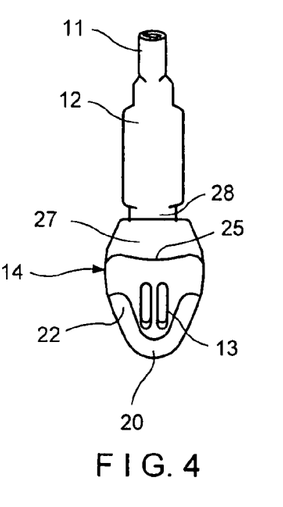
FIG. 4 is a front elevation.

For quick easy 'blind' (i.e. without the need for a laryngoscope) insertion of the device 10, the toe 20 in FIGS. 3 and 5, is shaped with an anterior curve 21 at an angle of about 15° towards the laryngeal opening surface of the toe 20. This upturned 'toe' 20 facilitates the negotiation of the device 10 at the level of posterior part of the tongue and nasopharynx.

The part of the chamber 14, extending from the ridge 24 to the toe 20 is in the form of a concavity with lateral ribs 22, which in cross-section is crescent shaped. The purpose is twofold. With insertion, the shape tends to allow for the epiglottis to escape being picked up and dragged downwards, producing downfolding and obstruction. The other purpose is that the entrance to the oesophagus is crescent-shaped with the anterior to the oesophagus positioned larynx providing the reason for the concave aspect of the crescent. As such there is a better downward seal without a marked oesophageal dilatation, which tends to cause epiglottic closure.

For quick easy 'blind' (i.e. without the need for a laryngoscope) insertion of the device, it may be necessary to use an introducer (a stiff flexible curved rod) with its tip inserted into the device from the said first end as far as the toe 20, so that possible folding of the device is avoided.

In its preferred form, the device is manufactured by means of blow-molding a grade of soft thermoplastic with rubbery characteristics and is blow molded into the shape described and illustrated in the drawings. The use of suitable resilient flexible materials will allow the devices to retain their shape without causing excessive pressure against the pharyngeal walls when in position. The device can thus be manufactured at minimal cost and is intended for a single use.

It is desirable that the stem 12 enters the saccular portion 14 at an appropriate angle to conform to the shape of the pharynx and outlet via the mouth. In order that this be achieved, a measure of flexibility is required and achieved at the junction 19 by means of an oval or rounded rectangular cross-section of the stem 12. In order to improve the flexing at the point 19 where the stem meets the chamber, the cross-section of the stem is reduced at 28.

As the device 10 is hollow, there is capacity for placement of porous hydrophobic material or other filter elements within the saccular chamber 14 to provide heat and moisture exchange within the device and filtration.

Figure 6:
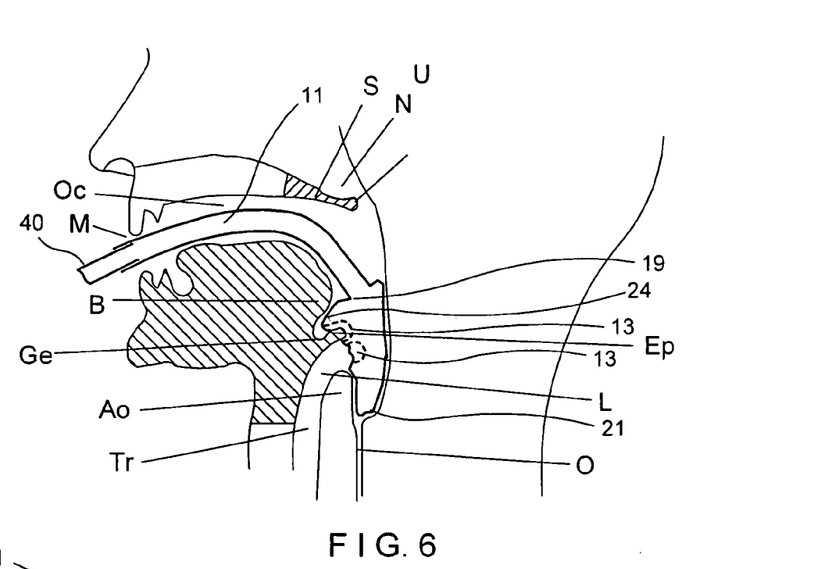
FIG. 6 is a sectional side elevation of a second embodiment of the airway device in relation to the anatomy of a patient.
Figure 7:
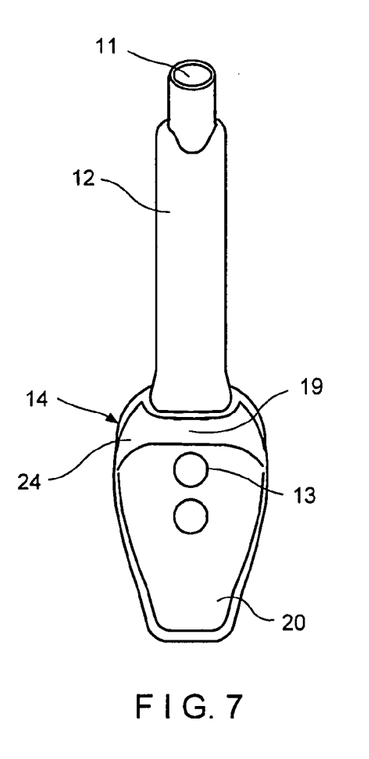
FIG. 7 is a front elevation of the device in FIG. 6.
Figure 8:
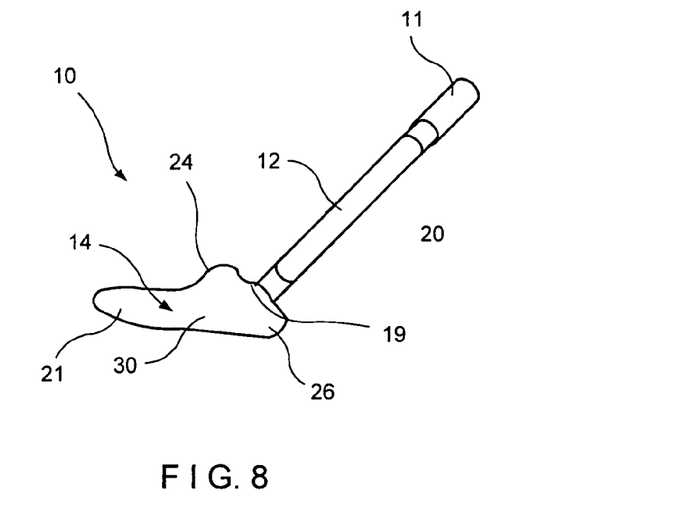
FIG. 8 is a side elevation.

The device shown in FIGS. 6 to 8 is substantially similar to the one shown in FIGS. 1 to 5 and described above. It differs to the extent that the stem is joined to the chamber 14 just above the ridge 24 so that in use access to the throat and tonsillar region is possible.

Figure 9:
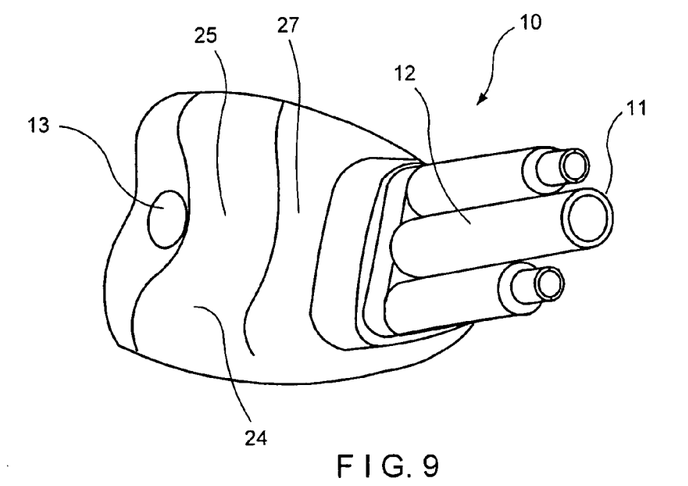
FIG. 9 is a perspective view of a 'truncated' form of the device from above.
Figure 10:
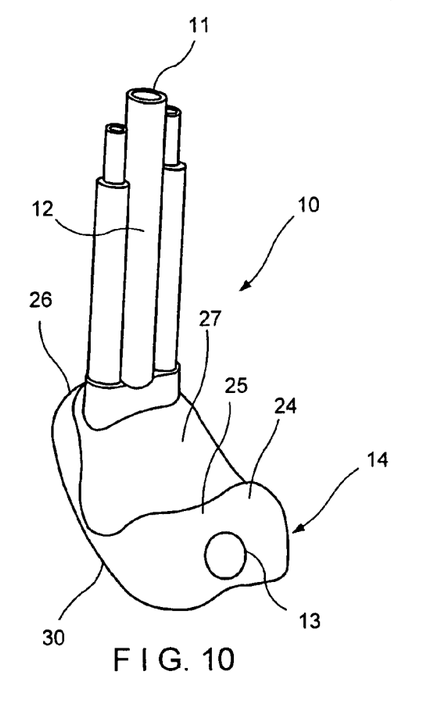
FIG. 10 is a perspective view from the front and FIG. 11 is a side elevation.
Figure 11:
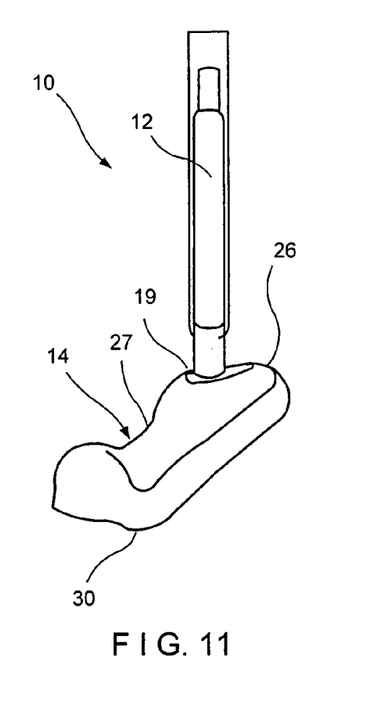
Figure 12:
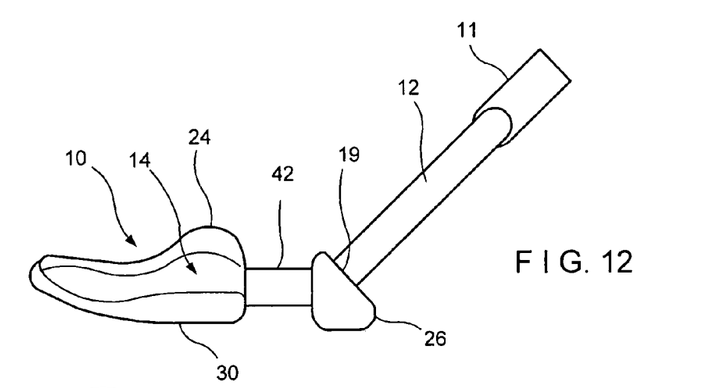
FIG. 12 is a side elevation of an alternative form of the device and FIG. 13 is a rear elevation and FIGS. 14 and 15 represent another variant of the same form.
Figure 13:
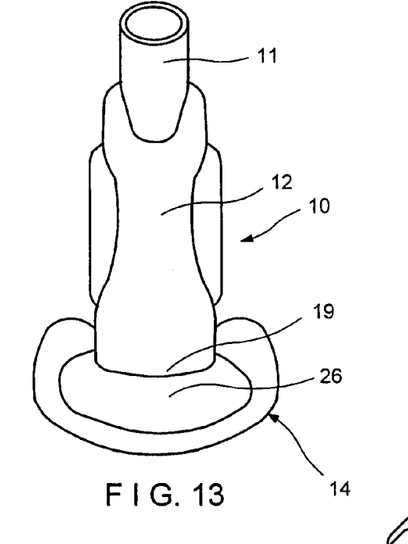
Figure 14:
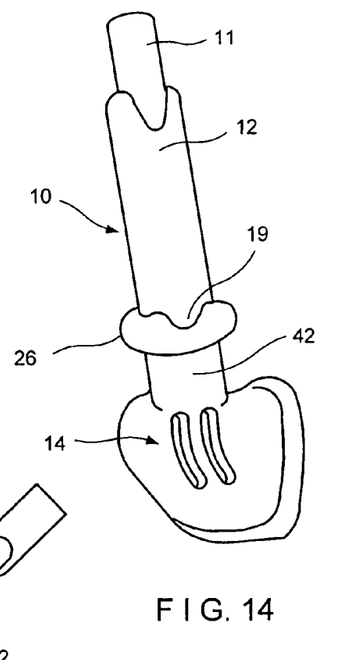
Figure 15:
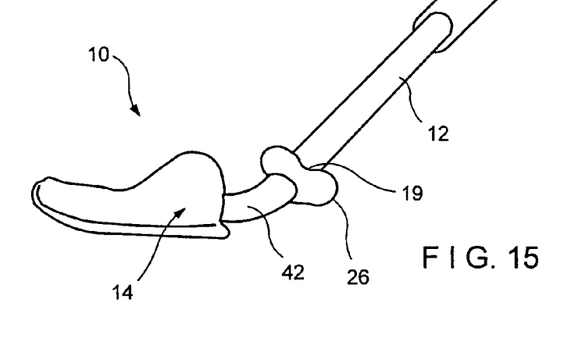

Alternatively, in FIGS. 9-11, an artificial airway device 10, for use in place of an endotracheal tube to facilitate ventilation of the lung in unconscious patients, is in the form of a pharyngeal outlet obturator airway 10 or POOBAIR. It differs from the device described in FIGS. 1 to 5 in that the toe 20 has been truncated, and accordingly does not offer the advantage of being able to provide the downward seal to the oesophagus. It offers the one advantage of not requiring such deep insertion and therefore is less stimulatory and may be more tolerable at lighter planes of anaesthesia.

The chamber 14 in use forms an upward-outlet-from-the-pharynx gas tight seal at the zone 24,25 in the space that extends from the base of the tongue or glossoepiglottic fold GE and the two pyriform fossae in the anterior aspect that correspond with the two lumps 24, the lateral and posterior pharyngeal walls and extending to the toe 20 of the chamber 14 that corresponds to the nasopharynx N and soft palate S.

The two embodiments of the device as shown in FIGS. 12 and 13, and 14 and 15 have a narrowed neck 42 between the body of the saccular chamber 14 and the heel 26. As shown in FIGS. 12-15 the advantage of the heel 26 is retained which is adapted to engage in the nasal pharynx. The advantage of these embodiments is that they can be used in cases where the patient's tonsillar anatomy would preclude the use of the devices described above. They can also provide improved flexibility and simplify mould making.

Key to Anatomical Terms
Ao=Anterior Oesophageal Wall
B=Base of Tongue
Ep=Epiglottis
Ge=Glosso-epiglottic fold
Hp=Hard palate
L=Laryngeal opening
M=Mouth
Nc=Nasal cavity
N=Nasopharynx
O=Oesophagus
Oc=Oral cavity
P=Pharynx
Sp=Soft palate
Te=Teeth
T=Tongue
Tr=Trachea
U=Uvula

The invention claimed is:

1. An artificial airway device of a resilient material for use as a combined obturator and airway device without penetration into the larynx comprising a flexible pre-formed shaped saccular chamber designed to seal in the pharynx at the base of the tongue and having a semi-rigid hollow stem projecting from a position at or near one end of the chamber at an angle of 90° to 180° to the longitudinal axis of the said chamber, the chamber being provided with one or more openings, and dimensioned and arranged so that in use the chamber is adapted to sealingly engage in a patient's pharynx with at least one opening communicating with the laryngeal inlet and so that the stem extends into or through the patient's mouth for connection to a breathing circuit, wherein said saccular chamber is of a generally foot-like form whose upper face is provided with a transverse ridge extending between two lateral lumps to constitute a sealing zone which in use is arranged to conform to the shape of the base of the tongue and the pyriform fossae and to provide an effective seal of pharynx, and wherein corresponding indentations are formed on either side of the ridge in the upper face and lower face of the saccular chamber, dimensioned and arranged so that in use each pair of corresponding indentations abut each other in order to increase the rigidity of the chamber and the ridge and in use to prevent the collapse of the chamber.

2. A device as claimed in claim 1 wherein said upper face of the saccular chamber is generally concave along its length in order to better conform with the shape of a patient's pharynx, the concavity including a 'toe' end of the chamber so that on insertion it will not catch on the epiglottis at the base of the tongue and so that it will seal into a crescent shaped entrance into the oesophagus.

3. A device as claimed in claim 1, in which a tip or 'toe' end of the saccular chamber is dimensioned so that in use it protrudes beyond the laryngeal opening so that it extends into the entrance of the oesophagus in order to prevent gas from entering the stomach.

4. A device as claimed in claim 1, in which the stem has a substantially rectangular section to enable it to flex in a plane through the longitudinal axis.

5. A device as claimed in claim 4, in which the relative stiffness of the stem compared with the chamber due to their relative wall thicknesses and the rectangular section of the stem at its entrance to the chamber causes the chamber to buckle resiliently at a foot of the stem without distorting the sealing surfaces when the stem is turned towards the perpendicular from the longitudinal axis of the chamber.

6. A device as claimed in claim 1, in which the 'heel' end of the chamber is provided with a bulb or lobe extending beyond a point where the stem enters the saccular chamber, and so dimensioned and arranged so that in use it engages into the patient's nasal-pharynx in order to hold the device in the required position.

7. A device as claimed in claim 1, in which the under-side of the toe end of the saccular chamber is upwardly angled at about 15° to 30° to the longitudinal axis, over 15 to 30% of the length of the chamber, to ease insertion of the device into a patient's pharynx.

8. A device as claimed in claim 1, in which the chamber is provided with a neck between a main body thereof and a portion adjoining the stem, so that the device has improved flexibility and in use the neck allows for unusual pharyngeal tonsillar anatomy.

9. A device as claimed in claim 1, in which one or more openings are provided on a forward or upper face so that in use they are arranged to collect any liquid into the chamber and by acting as a liquid trap thus prevent the liquid from entering the patient's larynx, trachea or lungs.

10. A device as claimed in claim 9 in which an axial longitudinal bar is provided through one of the openings which in use communicates with the laryngeal opening, in order to minimise the risk of a catheter inserted into the device form passing through the opening that communicates with the larynx.

11. A device claimed in claim 9, in which the saccular chamber is truncated at a toe portion so that in use it does not penetrate the oesophagus and accordingly does not require such deep insertion to make it more tolerable at lighter planes of anaesthesia.

12. A combined airway and obturator device for sealing a patient's pharynx during anaesthesia without penetration of the device into the larynx, the device comprising:

(i) a body of resilient material defining an elongate flexible saccular chamber, the body having a leading end and a trailing end and being bounded by first and second opposed elongate surfaces, the first surface having a raised ridge across it, the ridge being shaped to conform with the shape of the base of the tongue adjacent the glossoepiglottic fold to seal against the base of the tongue, wherein the first surface includes a pair of laterally spaced lumps, the ridge extending transversely across the first surface between said pair of laterally spaced lumps, and the second surface is shaped so as sealingly to contact the back of the patient's throat whereby the pharynx is sealed;

(ii) an opening in said body, the opening being on one side of said ridge and serving to place said chamber in communication with the laryngeal inlet of a patient; and (iii) a hollow stem protruding from the chamber at the trailing end of the chamber for connecting the interior of the chamber, thorough the mouth of the patient, to an external ventilation apparatus, the stem being at an angle of between 90 and 180 degrees with respect to the direction of elongation of the chamber.

13. A device as claimed in claim 12, in which said lumps project slightly from the ridge.

14. A device as claimed in claim 13, in which the first surface of the saccular chamber is generally concave along its length in order to better conform with the shape of a patient's pharynx, the said concavity including the leading end of the chamber so that on insertion it will not catch on the epiglottis at the base of the tongue and so that it will seal into the crescent shaped entrance into the oesophagus.

15. A device as claimed in claim 13, in which corresponding indentations are formed on either side of the ridge in the first surface and in the second surface of the saccular chamber, dimensioned and arranged so that in use each pair of corresponding indentations abut each other in order to increase the rigidity of the chamber and the ridge and in use to prevent the collapse of the chamber.

16. A device as claimed in claim 12, in which the first surface of the saccular chamber is generally concave along its length in order to better conform with the shape of a patient's pharynx, the said concavity including the leading end of the chamber so that on insertion it will not catch on the epiglottis at the base of the tongue and so that it will seal into the crescent shaped entrance into the oesophagus.

17. A device as claimed in claim 16, in which corresponding indentations are formed on either side of the ridge in the first surface and in the second surface of the saccular chamber, dimensioned and arranged so that in use each pair of corresponding indentations abut each other in order to increase the rigidity of the chamber and the ridge and in use to prevent the collapse of the chamber.

* * * * *